United States Patent [19]

Roberts et al.

[11] Patent Number: 5,369,997
[45] Date of Patent: Dec. 6, 1994

[54] ACTIVE DOUBLET METHOD FOR MEASURING SMALL CHANGES IN PHYSICAL PROPERTIES

[75] Inventors: Peter M. Roberts; Michael C. Fehler, both of Los Alamos; Paul A. Johnson; W. Scott Phillips, both of Santa Fe, all of N. Mex.

[73] Assignee: The United States of America as represented by the United States Department of Energy, Washington, D.C.

[21] Appl. No.: 310

[22] Filed: Jan. 4, 1993

[51] Int. Cl.$^5$ .................. G01N 29/04; G01R 33/20
[52] U.S. Cl. .................................................. 73/598
[58] Field of Search .............. 73/598, 600, 602, 648, 73/646, 659

[56] References Cited

U.S. PATENT DOCUMENTS 5,095,465  3/1992  Stokoe II .......................... 73/598

OTHER PUBLICATIONS

G. Poupinet et al., "Monitoring Velocity Variations in the Crust Using Earthquake Doublets: An Application to the Calaveras Vault, California," 89 J. Geophys. Res., No. B7, pp. 5719-5731 (July 1984).

Primary Examiner—Richard E. Chilcot, Jr.
Assistant Examiner—William L. Oen
Attorney, Agent, or Firm—Ray G. Wilson; William A. Eklund; William R. Moser

[57] ABSTRACT

Small changes in material properties of a work piece are detected by measuring small changes in elastic wave velocity and attenuation within a work piece. Active, repeatable source generate coda wave responses from a work piece, where the coda wave responses are temporally displaced. By analyzing progressive relative phase and amplitude changes between the coda wave responses as a function of elapsed time, accurate determinations of velocity and attenuation changes are made. Thus, a small change in velocity occurring within a sample region during the time periods between excitation origin times (herein called "doublets") will produce a relative delay that changes with elapsed time over some portion of the scattered waves. This trend of changing delay is easier to detect than an isolated delay based on a single arrival and provides a direct measure of elastic wave velocity changes arising from changed material properties of the work piece.

13 Claims, 6 Drawing Sheets

ACTIVE DOUBLET METHOD FOR MEASURING SMALL CHANGES IN PHYSICAL PROPERTIES

BACKGROUND OF THE INVENTION

This invention generally relates to nondestructive evaluation and, more particularly, to measuring small changes occurring within a volume of material as an effect on the propagation of waves within the volume. This invention is the result of a contract with the Department of Energy (Contract No. W-7405-ENG-36).

A significant problem in the field of nondestructive evaluation (NDE) is detecting progressive small changes in material properties that can lead to catastrophic events, e.g., the fatigue failure of bridges or airplane wings. Traditionally, the use of acoustic signals to characterize elastic properties of engineering materials has relied primarily on direct-path measurements of travel time and wave amplitude of the first arriving signal. Travel time ultrasonic tomography can provide redundant signals and yield images of velocity structures within materials, but the spatial extent and resolution of these images are limited by the number of sources and receivers used to generate and collect the necessary waveform data. The precision with which travel-time measurements can be made is limited by the timing precision of the recording instruments used and by the noise in the signals.

In areas that use seismic signals to characterize physical properties of rocks, low resolution imaging of volumes with few source-receiver pairs can be achieved by using the redundancy properties of coda waves, i.e., late-arriving scattered acoustic waves, whereby the late-arriving waves have sampled larger regions of material surrounding the source and receiver. Coda waves generated by natural earthquakes have been used to determine material properties in various regions of the earth. Progressive phase delays between coda waves generated by nearly identical pairs of natural earthquakes (called doublets) which occur at different times in the same location have been analyzed to determine local changes in seismic velocity occurring in the time interval between earthquakes.

There has been substantial analytical work done using natural seismic sources, e.g., earthquakes. See, e.g., Poupinet et al., "Monitoring Velocity Variations in the Crust Using Earthquake Doublets: An Application to the Calaveras Fault, California," J. Geophys. Res., 89:5719-5731 (1984). There has, however, been little extension of this work because (1) naturally occurring doublets are hard to find; (2) even when natural doublets are found, there is no guarantee that the source locations are absolutely identical for both events, leading to ambiguous interpretations of measured phase delays; and (3) the algorithm used is not robust and requires substantial user interaction due to inherent instabilities and ambiguities in phase-delay estimates.

The present invention has recognized that the doublet method has important applications to high sensitivity NDE of commercial products, both on a production basis and over extended periods of time, since the technique is capable of analyzing a bulk volume of a work piece. Accordingly, it is an object of the present invention to detect small changes in bulk material properties as an early indication of changes in material strength and fatigue life.

Another object of the present invention is to detect changes occurring over volumes of material rather than along a single line-of-sight path.

One other object of the present invention is to eliminate source location ambiguities.

Still another object of the present invention is to improve the stability of the analysis algorithm using the doublet response detected at the receiver transducers.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects, and in accordance with the purposes of the present invention, as embodied and broadly described herein, the method of this invention enables the measurement of small changes in the physical properties of a work piece. A first mounting is provided for a first source transducer and a first receiver transducer on the work piece. The work piece is interrogated by a first pulse input from the first source transducer to generate a first response received by the first receiver transducer. A second mounting is provided for second source transducer and a second receiver transducer on said work piece, where the second mounting, the second source transducer, and the second receiver transducer are substantially identical with the first mounting, the first source transducer, and the first receiver transducer, respectively. The work piece is interrogated with a second pulse input from the second source transducer to generate a second response received by the second receiver transducer, where the second pulse is temporally displaced from the first pulse. The relative phase and amplitude changes along the coda portion of the first and second responses are determined to detect a physical change in the work piece.

BRIEF DESCRIPTION OF THE DRAWINGS

The accompanying drawings, which are incorporated in and form a part of the specification, illustrate an embodiment of the present invention and, together with the description, serve to explain the principles of the invention. In the drawings.

DETAILED DESCRIPTION OF THE INVENTION

Figure 1:
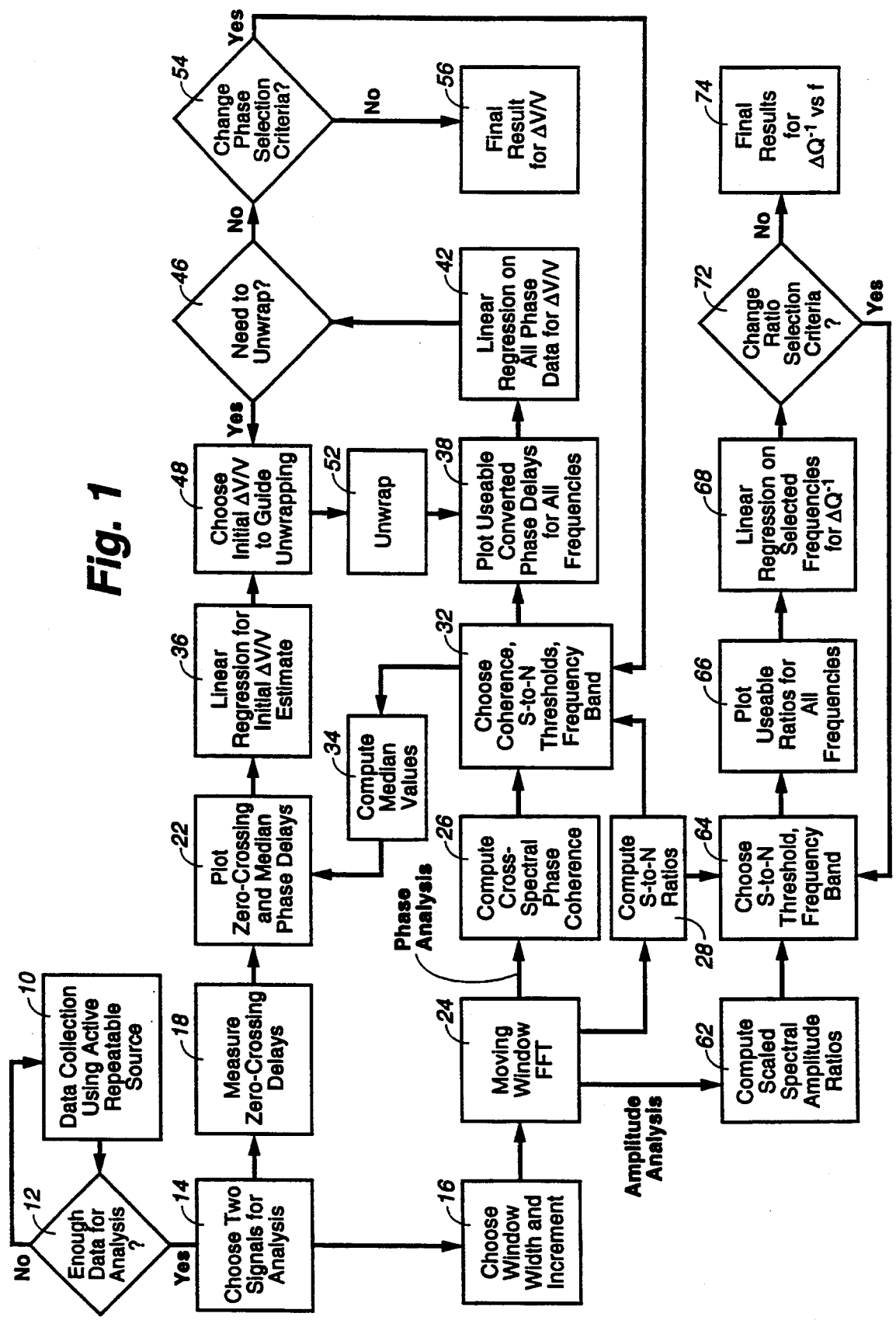
FIG. 1 is a block flow diagram of a doublet phase and amplitude analysis according to the present invention.

In accordance with the present invention small changes in elastic wave velocity and attenuation within a workpiece are determined through the use of active, repeatable sources for generating coda wave responses in a work piece, where the coda wave responses are temporally displaced. By analyzing progressive relative phase and amplitude changes between the coda wave responses as a function of elapsed time, accurate determinations of velocity and attenuation changes are made. Thus, a small decrease in velocity occurring within a sample region during the time periods between excitation origin times (herein called "doublets" since only a pair of excitations is compared) will produce a relative delay that increases with elapsed time over some portion of the scattered waves. If the velocity change is pervasive, the relative delay will increase linearly over the entire coda. This trend of increasing delay is easier to detect and measure than an isolated delay based on a single arrival.

In order to obtain a doublet suitable for the present analysis, source and receiver transducers are mounted on a selected workpiece and a first response is generated. The response is a direct arrival of the transmitted excitation pulse, i.e., a line-of-sight response, followed by the coda, the waves that are scattered throughout the volume of the work piece and arrive at various delay times at the receiver transducer. At a later time, source and receiver transducers are again mounted on the work piece and a second response is generated.

The first and second responses are generated and acquired using source and receiver transducers having substantially identical characteristics, and reproducible source-receiver geometry and coupling to the sampled medium. Preferably the source and receiver transducers are mounted permanently to the work piece to assure the required identity. It will be appreciated that the present technique is developed to detect small changes occurring in the sampled volume and the mechanism by which scattered waves are generated cannot vary significantly, i.e., velocity changes on the order of 5% or smaller.

In general, any type of source and receiver transducers can be used as long as the same ones, or others with identical response characteristics, are used to obtain each test signal. It is not necessary, however, for the source transducer to be identical with the receiver transducer. Regardless of how the signals are generated, the most important source and receiver characteristic to maintain is the phase spectrum of the impulse response for each device used. This ensures that any frequency-dependent phase shifts introduced by the source or receiver will cancel out when the doublet analysis is applied. The amplitude response is of little importance because signals can be scaled to match each other in amplitude as long as the signal-to-noise ratio is acceptable.

Further, almost any input source shape can be used as long as the same function is used every time. However, the interpretation of measured phase delays is simplified when the source is a discrete pulse. This allows scattered waves to be modeled as a superposition of individual wavelets arriving at the receiver at progressively later times that correspond to progressively longer travel paths within the test medium. Control of the source shape is easier to achieve when using piezo-electric transducers, rather than explosive sources or laser ablation.

The requirements for coupling of the source and receiver to the test medium apply to both transducer location and the physical bonding used for attachment. Slight changes in transducer location can produce phase delays that mimic velocity changes in the medium. Changes in the bond between the transducer and the medium can effectively cause changes in the source or receiver response that are often difficult to characterize. Although the specific method used to locate and attach transducers is irrelevant, it is necessary to establish a reproducible bonding procedure in cases where transducers are not permanently mounted to the work piece.

Preferably the same data acquisition equipment is used to collect each test signal because the response characteristics of electronic devices vary considerably from instrument to instrument. If the same equipment is not used for each response signal, each signal must be corrected for any phase delays introduced by the equipment. This requires an accurate knowledge of the impulse response characteristics for each component in the data acquisition path. If possible, data should be acquired using repeated source firings and stacking of the resulting received time series to obtain each time signal. Signal stacking will increase the number of acceptable phase points that can be used and this will reduce the standard errors of the measured velocity changes.

As noted above, changes in the velocity of pulse propagation, V, in the work piece are indicative of material property changes in the work piece, e.g., a crack initiation, material work hardening, crystallization, etc. Since each signal pulse traverses the same volume of material, the relative signal delays in coda portions of temporally displaced pulses will provide a direct measure of the change in signal propagation velocity along each path, i.e., $\Delta V/V$, since the same distance will be traveled for identical points of the received signals. The value of $\Delta V/V$ is the slope of a plot of the change in received signal delay vs. elapsed time and is determined directly by the present invention.

Referring now to FIG. 1, there is shown a block flow diagram of the doublet phase and amplitude analysis. A work piece is interrogated 10 by an active repeatable source until it is determined 12 that there is enough data for an analysis. Two signals are selected 14 for analysis from different times of interrogation 10.

In one analysis, time delays in the coda signal are estimated 18 directly by measuring time differences between identical zero-crossings detected in the two signals. These are then plotted 22 to give an initial estimate of the delay trend versus elapsed time.

In another analysis, a moving window is selected 16 to increment through the selected signals 14. A fast Fourier transform (FFT) is then performed 24 on each signal at each time step as the window is incremented. For each pair of data windows, the cross-spectrum is obtained 26 by multiplying the Fourier transform of one signal by the complex conjugate of the other:

$$S_{12}(t,f) = S_1(t,f)S_2^*(t,f), \qquad (2)$$

where $S_1(t,f)$ and $S_2(t,f)$ are the Fourier transforms of the two windowed signals at elapsed time t.

For each cross-spectrum, relative phase delays are obtained at each frequency by computing the arctangent of the ratio of the imaginary part of $S_{12}(t,f)$ to the real part. Because the arctangent function has a modulo ($2\pi$) ambiguity, the cross-spectrum phase versus frequency must be correctly unwrapped 52 to allow phase delays larger than $+\pi$ or less than $-\pi$. Before unwrapping, the cross-spectral phase data for a given elapsed time, t, each phase value is first converted to units of equivalent time delay as $$\tau(t,f) = \phi(t,f)/2\pi f \qquad (1)$$

All phase-derived time delays are then plotted 38 directly versus elapsed time. This eliminates the need to inspect individual phase versus frequency plots at each time step. Thus, all usable data may be fit simultaneously to a linear regression 42 of an initial $\Delta V/V$ estimate. A coherence magnitude spectrum is also computed 26 using smoothed versions of the cross spectrum and autospectra in each time window.

From the moving window FFT 24 a signal-to-noise ratio is also calculated 28 and data is selected for analysis over a selected frequency band and having a signal-to-noise ratio and a coherence value above selected thresholds. A coherence threshold provides that the received waveforms are substantially identical with only phase delays arising from changes in material properties. The data points that are selected are then used to compute 34 median values of the phase-derived time delays and are provided to the initial data plot 22 along with the measured 18 zero-crossing delays. These are then used to perform an initial linear regression 36 to obtain an estimate 48 of $\Delta V/V$ used to guide phase unwrapping 52.

All selected data points are provided for use in plotting 38 phase-derived time delays for all frequencies. A linear progression 42 is then done on all phase data for $\Delta V/V$ and the data is examined to determine 46 whether there is a need to unwrap the data. If the phase-derived time delays have erroneously high or low values at higher frequencies, either the zero-crossing data or the median phase delays are used to unwrap 52 the selected data. To unwrap 52 the phase-derived time delays, multiples of 1/f are added or subtracted to the phase-derived time delays 38 until the adjusted values 42 lie as close as possible to the initial estimate 36. Once the unwrapping iterations are completed, the result is examined 54 for dispersive effects, e.g., effects arising from defects with sizes on the order of the wavelengths being used to test the material. If dispersive effects are observed, the frequency band is changed 32 to perform the $\Delta V/V$ regression over multiple frequency bands rather than fitting all frequencies simultaneously. The final result for $\Delta V/V$ is then output 56.

The attenuation of each signal is also computed from the moving window FFT 24. Scaled spectral amplitude ratios are computed 62 for the same data window pairs that were used to obtain cross-spectral phase. Signal-to-noise threshold and frequency bands are then selected for analysis. After taking the natural logarithm of the spectral ratios and scaling by 1/f all selected data are plotted 66 simultaneously versus elapsed time. The scaled spectral ratios can be represented as a function of elapsed time by the relation:

$$\ln\left[\left|\left|\frac{S_1(t,f)}{S_2(t,f)}\right|\right|\right]\frac{1}{f} = \frac{\ln[R_o(f)]}{f} + \pi t \Delta Q^{-1} \qquad (3)$$

where $S_1$ and $S_2$ are the Fourier transforms versus elapsed time and $R_o = \{S_1(0,f)\}/\{S_2(0,f)\}$ is the relative source term, which is unity in the case of doublets.

The slope of the regression line fit 68 to the data that obey this relationship is proportional to the attenuation change $\Delta Q^{-1}$. $\Delta Q^{-1}$ may be frequency dependent over certain bands and the ratio selection criteria may need to be changed 72 to provide separate fits over numerous frequencies to fully characterize an attenuation change to provide the final determination 74 of $\Delta Q^{-1}$ versus frequency.

To demonstrate the capabilities of the present method, identical source-receiver combinations were used to collect ultrasonic signals before and after altering the physical properties of two Plexiglas test samples, one $\frac{1}{2}$-inch thick plate and one $\frac{1}{4}$-inch thick plate. The transducers were placed in counterbored holes in the Plexiglas and affixed with epoxy. The source function inputs were half-cycle cosine pulses with pulse widths of 6.67 $\mu s$ for the thicker plate and 5.0 $\mu s$ for the thin plate. Scattered waves are generated by multiple reflections at the four edges of the Plexiglas plates.

Figure 2A:
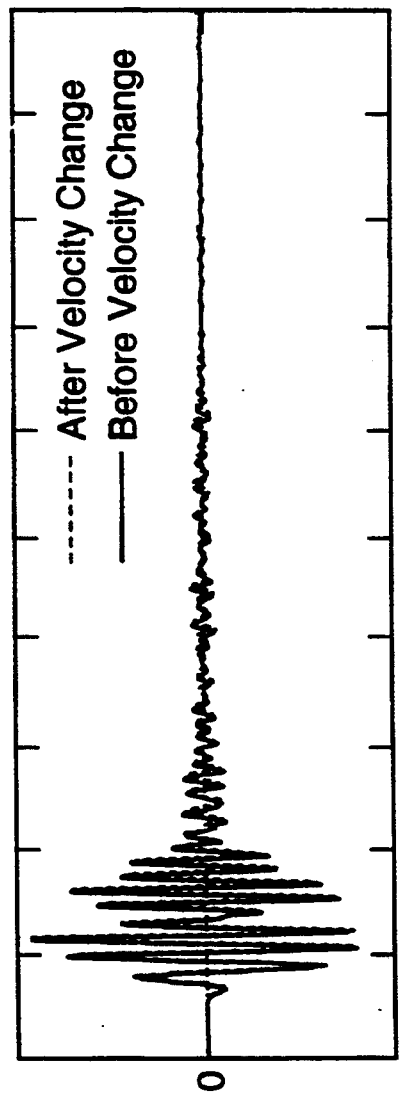
FIGS. 2A and 2B graphically depict a received doublet signal pair before and after a change in velocity through a work piece and the result of application of the processing steps shown in FIG. 1 for determining initial slope estimates used for adjusting the phase for modulo ($2\pi$) ambiguities.
Figure 2B:
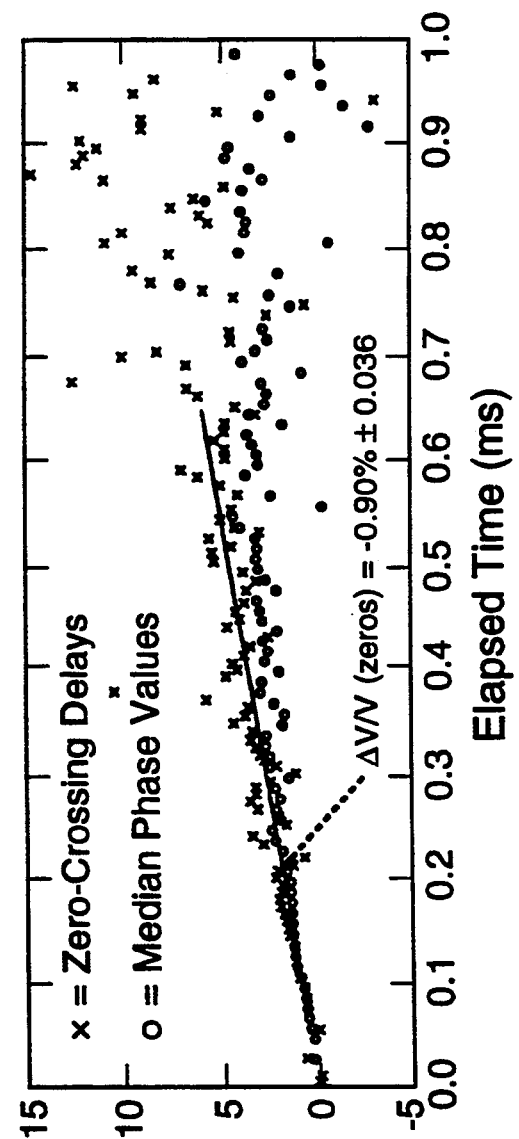

FIG. 2A graphically depicts doublet signals before and after a time interval during which the ambient temperature of the laboratory and concomitant temperature of the work piece was changed. FIG. 2B depicts the relative delays calculated from zero-crossing delays and median values from phase-derived time delays. The initial estimate of velocity change was obtained by linear regression of the zero-crossing values. It should be noted that the median phase delays underestimate the true delays at later elapsed times because the individual phase values in each time window have not been unwrapped yet.

Figure 3:
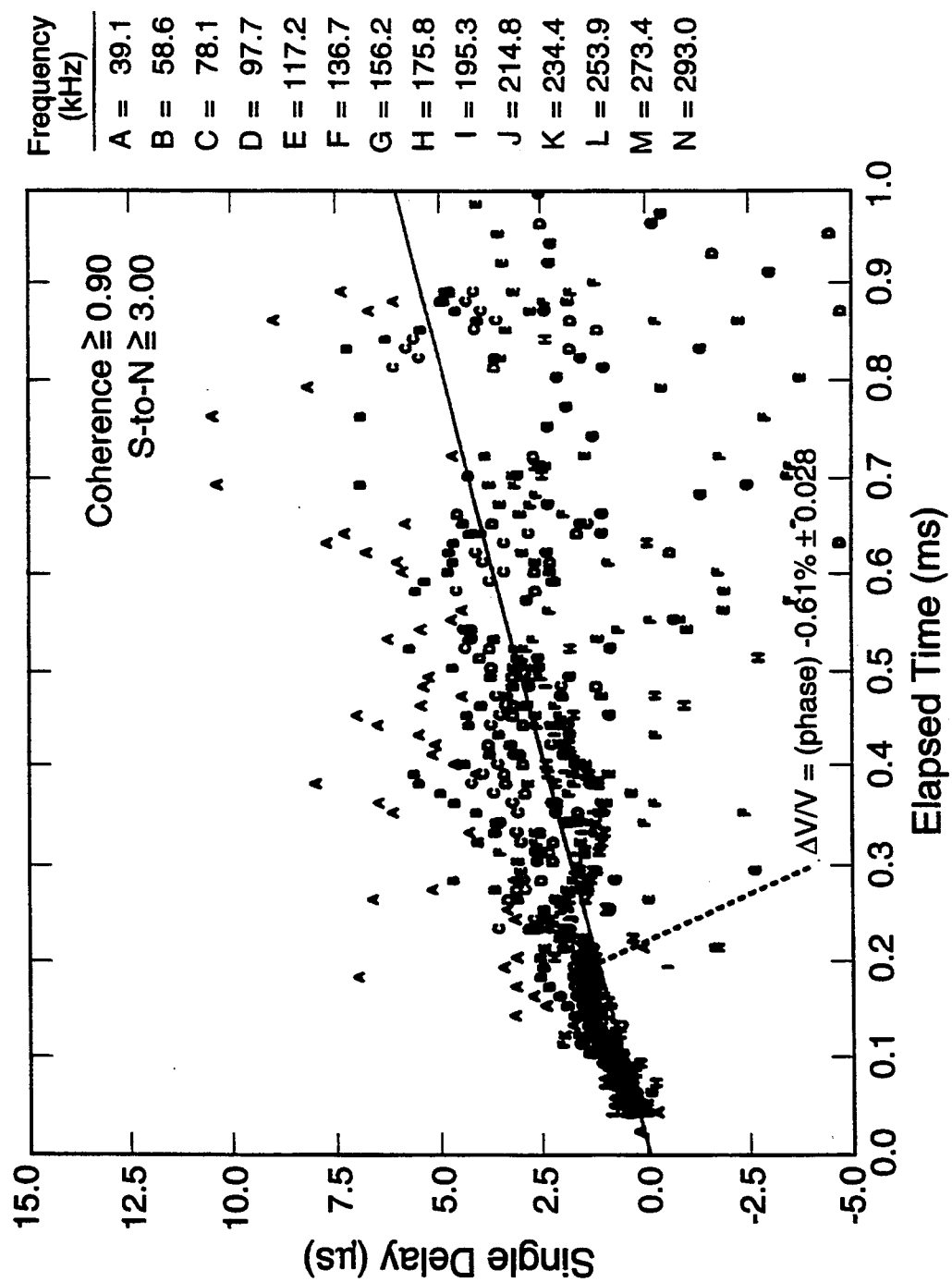
FIG. 3 graphically depicts cross-spectral phase points converted to equivalent time delay prior to unwrapping the phase points.

FIG. 3 depicts cross-spectral phase points converted to equivalent time delays and coded by frequency as shown in the figure. Phase points have not yet been unwrapped and this leads to an erroneously low estimate for the velocity change as seen by comparing the linear regression with the zero-crossing estimate shown in FIG. 2B.

Figure 4:
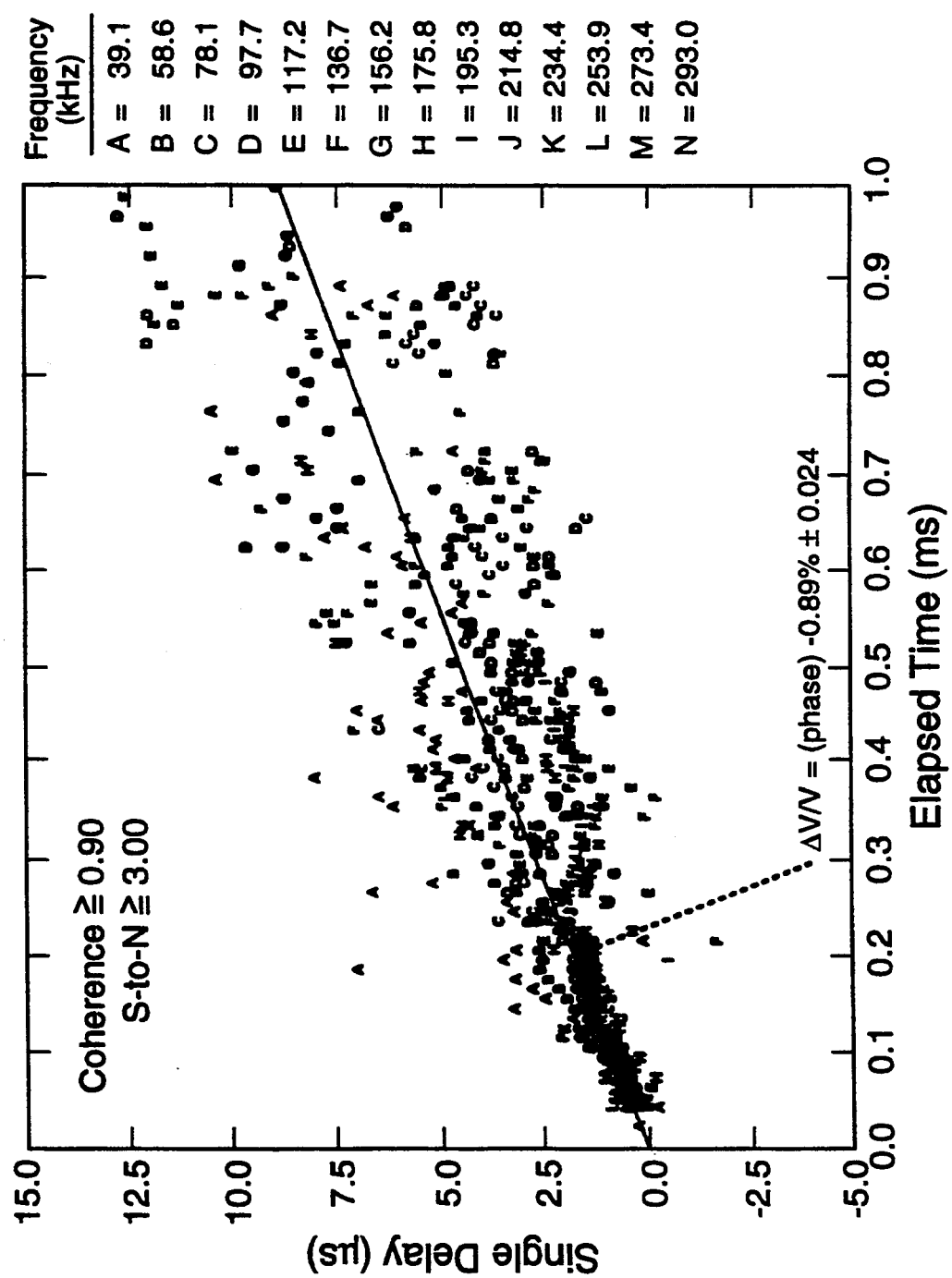
FIG. 4 graphically depicts the cross-spectral phase points shown in FIG. 3 after one iteration of phase unwrapping.

After one iteration of phase unwrapping using the velocity changes estimated from zero-crossing as guidance, the adjusted phase delays are shown in FIG. 4. Each phase point is adjusted by multiples of $2\pi$ until it lies as close as possible to the initial estimate. The resulting linear regression on the unwrapped phase yields a velocity change similar to the zero-crossing estimate, but the standard error is significantly lower.

Figure 5:
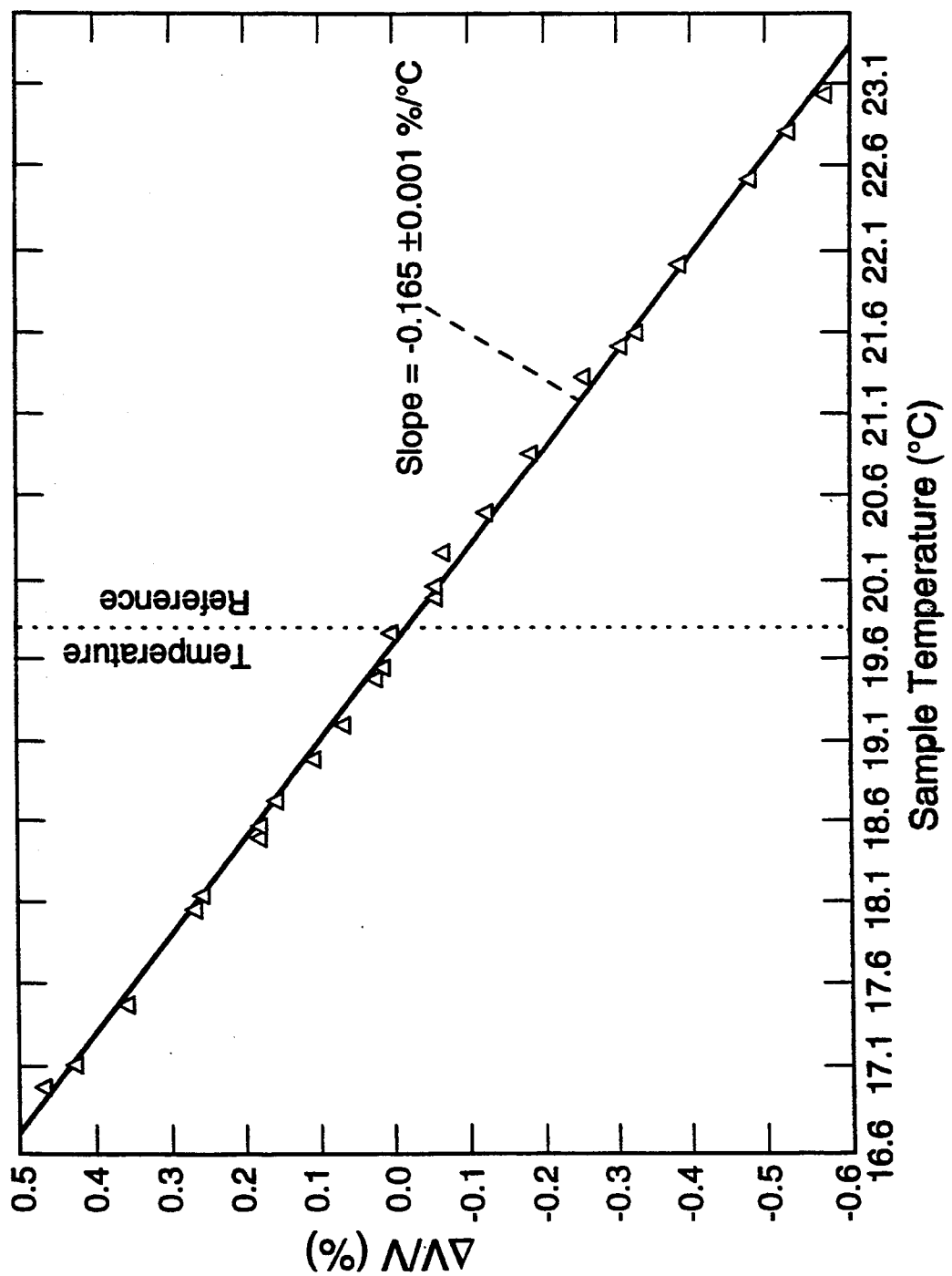
FIG. 5 graphically shows measured velocity changes in a Plexiglas sample versus ambient sample temperature for numerous doublet pairs.

The sensitivity of the doublet analysis and the reliability of the algorithm is graphically shown in FIG. 5, which shows measured velocity changes in the Plexiglas sample versus ambient sample temperatures for numerous doublet pairs. The smallest nonzero velocity changes in FIG. 5 has a value of 0.01% with a standard error of $\pm 0.001\%$. The slope of $-0.165\%/°$ C. obtained for velocity variations versus temperature is within the range of possible combined values for Plexiglas: about $-0.01\%/°$ C. for thermal expansion and $-0.15\%/°$ C. for the effects due to modulus and density changes.

Figure 6A:
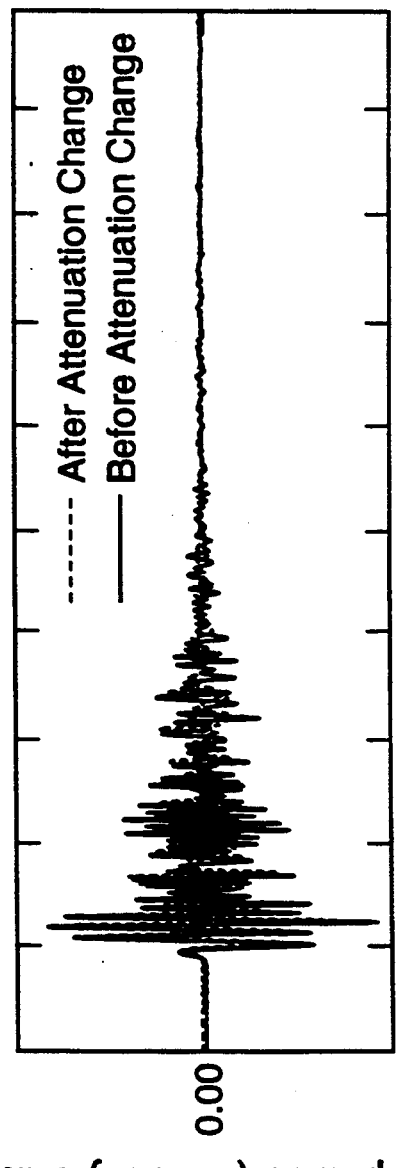
FIGS. 6A and 6B graphically depict received doublet signals before and after a change in attenuation in a work piece with spectral amplitude ratios plotted for each time window to provide an estimate of the attenuation changes.
Figure 6B:
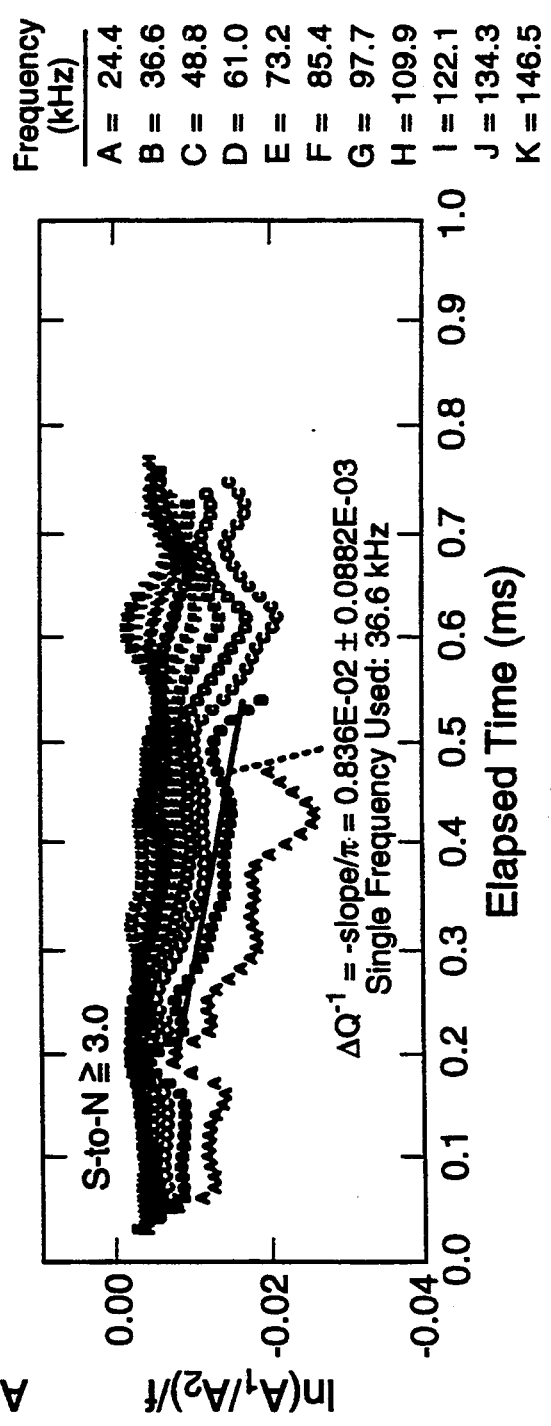

FIGS. 6A and 6B show a doublet test signal pair and resulting amplitude attenuation analysis, respectively, for a Plexiglas test sample. The doublet signal pair was obtained before and after permanently damaging the sample by exposure to extreme heat followed by cooling back to ambient temperature. Spectral amplitude ratios, shown in FIG. 5B, scaled by 1/f, are plotted for each time window and coded by frequency. The slope of a line fit to decaying portions of the ratio curves yields an estimate of the attenuation change $\Delta Q^{-1}$. In this case, the change is frequency dependent because the slope varies with frequency. An example of the linear regression for a single frequency at 36.6 kHz is illustrated. Thus, the present invention provides a new NDE technique for detecting small changes in material properties related to elastic wave velocity and signal attenuation by using active repeatable sources to produce doublets in a work piece. An improved analysis method then provides a robust method for sensitively determining changes in elastic wave velocity. The method is also extended to using relative amplitude decay rates for measuring small changes in attenuation $Q^{-1}$. Laboratory experiments in Plexiglas have demonstrated that the improved phase delay algorithm can detect velocity changes as small as 0.01%. The amplitude-decay method was also used to measure changes in attenuation $\Delta Q^{-1}$ as small as about 10%. Both of these measurements are sensitive precursors to changes in material properties that affect the strength and fatigue life of a work piece.

The foregoing description of a preferred embodiment of the invention has been presented for purposes of illustration and description. It is not intended to be exhaustive or to limit the invention to the precise form disclosed, and obviously many modifications and variations are possible in light of the above teaching. The embodiment was chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A method for measuring small changes in the physical properties of a work piece, comprising the steps of:
    providing a first mounting of a first source transducer and a first receiver transducer on said work piece;
    interrogating said work piece by a first pulse input from said first source transducer to generate a first response received by said first receiver transducer;
    providing a second mounting of a second source transducer and a second receiver transducer on said work piece, where said second mounting, said second source transducer, and said second receiver transducer are substantially identical with said first mounting, said first source transducer, and said first receiver transducer, respectively;
    interrogating said work piece with a second pulse input from said second source transducer to generate a second response received by said second receiver transducer, where said second pulse is temporally displaced from said first pulse; and
    determining the relative phase and amplitude changes along the coda portion of said first and second responses to detect physical changes in said work piece.

2. A method according to claim 1, wherein said first and second receivers have substantially identical phase spectra for an impulse response.

3. A method according to claim 1, wherein said first and second pulse inputs are discrete pulses.

4. A method according to claim 1, wherein said second mounting, said second source transducer, and said second receiver transducer are said first mounting, said first source transducer, and said first receiver transducer.

5. A method according to claim 2, wherein said first and second pulse inputs are discrete pulses.

6. A method according to claim 4, wherein said first and second pulse inputs are discrete pulses.

7. A method according to claim 4, wherein said first and second receivers have substantially identical phase spectra for an impulse response.

8. A method according to claim 7, wherein said first and second pulse inputs are discrete pulses.

9. A method according to claim 1, wherein the step of determining said relative phase and amplitude changes further comprises the steps of measuring time differences between identical zero-crossings in said first and second responses to provide an estimate of change in signal delay versus elapsed time.

10. A method according to claim 9, wherein the steps of determining said relative phase and amplitude changes further includes the steps of:
    incrementing a time window through each one of said first and second responses;
    performing a FFT on said first and second response signal within each said time window;
    obtaining a cross-spectral phase coherence between the FFT's for said response signal for identical ones of said window in each one of said first and second responses; and
    computing relative phase delays between said first and second responses from said cross-spectral phase coherence.

11. A method according to claim 10, further comprising the steps of:
    determining an initial value of $\Delta V/V$ from said signal delays determined from said zero-crossings; and
    applying said initial value of $\Delta V/V$ to said relative phase delays from said cross-spectral phase coherence to determine phase delay values greater than $\pm \pi$; and
    shifting said relative phase delays as needed to include $\pm \pi$ values.

12. A method according to claim 11, further comprising the step of performing a linear regression on said shifted phase delays to from a final value of $\Delta V/V$.

13. A method according to claim 1, further including the steps of:
    incrementing a time window through each one of said first and second responses;
    performing a FFT on said first and second response signal within each said time window;
    obtaining a cross-spectral phase coherence between the FFT's for said response signal for identical ones of said window in each one of said first and second responses; and
    computing relative phase delays between said first and second responses from said cross-spectral phase coherence.

* * * * *